US008512712B2

(12) United States Patent
Morris et al.

(10) Patent No.: US 8,512,712 B2
(45) Date of Patent: Aug. 20, 2013

(54) REOVIRUS CLEARANCE OF RAS-MEDIATED NEOPLASTIC CELLS FROM MIXED CELLULAR COMPOSITIONS

(75) Inventors: Donald Morris, Calgary (CA); Bradley G. Thompson, Calgary (CA); Matthew C. Coffey, Calgary (CA)

(73) Assignee: Oncolytics Biotech Inc., Calgary, Alberta, CA (US)

(*) Notice: Subject to any disclaimer, the term of this patent is extended or adjusted under 35 U.S.C. 154(b) by 0 days.

(21) Appl. No.: 13/408,478

(22) Filed: Feb. 29, 2012

(65) Prior Publication Data

US 2012/0225045 A1    Sep. 6, 2012

Related U.S. Application Data

(60) Continuation of application No. 12/726,002, filed on Mar. 17, 2010, now Pat. No. 8,147,845, which is a division of application No. 11/807,930, filed on May 30, 2007, now Pat. No. 7,727,534, which is a continuation of application No. 11/236,059, filed on Sep. 26, 2005, now Pat. No. 7,431,932, which is a continuation of application No. 09/847,356, filed on May 3, 2001, now Pat. No. 6,994,858.

(60) Provisional application No. 60/268,054, filed on Feb. 13, 2001, provisional application No. 60/205,389, filed on May 19, 2000, provisional application No. 60/201,990, filed on May 3, 2000.

(51) Int. Cl.

| A61K 35/14 | (2006.01) |
| A61K 38/16 | (2006.01) |
| A61K 39/12 | (2006.01) |
| A61K 39/38 | (2006.01) |
| A61K 39/385 | (2006.01) |
| A61K 49/00 | (2006.01) |
| C12N 5/00 | (2006.01) |
| C12N 5/02 | (2006.01) |
| C12N 5/08 | (2006.01) |
| C12N 5/10 | (2006.01) |
| C07K 14/00 | (2006.01) |
| C07K 16/00 | (2006.01) |

(52) U.S. Cl.
USPC ... 424/215.1; 424/9.1; 424/184.1; 424/193.1; 424/196.11; 424/204.1; 435/325; 435/363; 435/366; 435/372; 530/350; 530/380; 530/386; 530/387.7; 530/388.15; 530/388.3

(58) Field of Classification Search
None
See application file for complete search history.

(56) References Cited

U.S. PATENT DOCUMENTS

| 4,576,928 | A | 3/1986 | Tani et al. |
| 5,514,340 | A | 5/1996 | Lansdorp et al. |
| 5,585,096 | A | 12/1996 | Martuza et al. |
| 5,637,677 | A * | 6/1997 | Greene et al. ............... 530/333 |
| 5,801,029 | A | 9/1998 | McCormick |
| 5,837,512 | A | 11/1998 | Rabson et al. |
| 5,840,502 | A | 11/1998 | van Vlasselaer |
| 5,861,159 | A | 1/1999 | Pardoll et al. |
| 6,136,307 | A | 10/2000 | Lee et al. |
| 6,184,043 | B1 * | 2/2001 | Fodstad et al. ............... 436/526 |
| 6,475,481 | B2 | 11/2002 | Talmadge |
| 6,528,057 | B1 | 3/2003 | Ambrus et al. |
| 6,596,268 | B1 | 7/2003 | Coffey et al. |
| 6,649,157 | B2 | 11/2003 | Coffey et al. |
| 6,994,858 | B2 | 2/2006 | Morris et al. |
| 7,192,580 | B2 | 3/2007 | Atkins et al. |
| 7,431,932 | B2 | 10/2008 | Morris et al. |
| 2002/0006398 | A1 | 1/2002 | Morris et al. |
| 2002/0037543 | A1 | 3/2002 | Atkins et al. |
| 2003/0044384 | A1 | 3/2003 | Roberts et al. |
| 2003/0165465 | A1 | 9/2003 | Roberts et al. |
| 2004/0109878 | A1 | 6/2004 | Atkins et al. |
| 2005/0026289 | A1 | 2/2005 | Morris et al. |

FOREIGN PATENT DOCUMENTS

| CA | 2283280 A1 | 2/1999 |
| EP | 0451611 A2 | 10/1991 |
| EP | 1344819 A2 | 9/2003 |
| WO | 9418992 A1 | 9/1994 |
| WO | 9425627 A1 | 11/1994 |
| WO | WO9908692 A1 | 2/1999 |
| WO | 9918799 A1 | 4/1999 |
| WO | 9945783 A1 | 9/1999 |
| WO | 0050051 A2 | 8/2000 |
| WO | 0135970 A1 | 5/2001 |

OTHER PUBLICATIONS

Colter et al. CD34+ Progenitor Cell Selection: Clinical Transplantation, Tumor Cell Purging, Gene Therapy, Ex Vivo Expansion, and Cord Blood Processing. J. Hematother. 5(2): 179-184, Apr. 1996.*
Adachi et al., A Midkine Promoter-based Conditionally Replicative Adenovirus for Treatment of Pediatric Solid Tumors and Bone Marrow Tumor Purging, Cancer Research, 61:7882-7888 (2001).
Andreansky et al., Evaluation of genetically engineered herpes simplex viruses as oncolytic agents for human malignant brain tumors, Cancer Research, 57:1502-9 (1997).
Armstrong et al., Studies on reovirus receptors of L cells: virus binding characteristics and comparison with reovirus receptors of erythrocytes, Virology, 138(1):37-48 (1984).
Bar-Eli et al., Preferential cytotoxic effect of Newcastle disease virus on lymphoma cells, J. Cancer Res. Clin. Oncol., 122(7):409-415 (1996).

(Continued)

Primary Examiner — Alana Harris Dent
(74) Attorney, Agent, or Firm — Kilpatrick Townsend & Stockton, LLP

(57) ABSTRACT

Reovirus can be used to selectively remove ras-mediated neoplastic cells from a cellular composition. It is of particular interest to purge autographs which may contain neoplastic cells with reovirus before transplanting the autographs back into the recipient, thereby reducing the risk of introducing or reintroducing neoplastic cells into the recipient.

22 Claims, 16 Drawing Sheets

(56) References Cited

OTHER PUBLICATIONS

Bashey et al., Proliferative but not nonproliferative responses to granulocyte colony-stimulating factor are associated with rapid activation of the p21ras/MAP kinase signalling pathway, Blood, 83(4):949-957 (1994).
Bensinger, Should we purge? Bone Marrow Transplant, 21(2):113-115 (1998).
Bischoff et al., An adenovirus mutant that replicates selectively in p53-deficient human tumor, Science, 274(5286):373-376 (1996).
Blagosklonny et al., In vitro evaluation of a p53-expressing adenovirus as an anti-cancer drug, Int. J. Cancer, 67(3):386-392 (1996).
Bos, Ras oncogenes in human cancer: a review, Cancer Res., 49(17):4682-4689 (1989).
Chandron et al., Protease cleavage of reovirus capsid protein μ1/μ1C is blocked by alkyl sulfate detergents, yielding a new type of infectious subvirion particle, J Virol., 72(1):467-475 (1998).
Chang et al., The E3L gene of vaccinia virus encodes an inhibitor of the interferon-induced, double-stranded RNA-dependent protein kinase, Proc. Nat. Acad. Sci., 89(11):4825-4829 (1992).
Chang et al., Identification of a conserved motif that is necessary for binding of the vaccinia virus E3L gene products to double-stranded RNA, Virology, 194(2):537-547 (1993).
Chang et al., Rescue of vaccinia virus lacking the E3L gene by mutants of E3L, J. Virol., 69(10):6605-6608 (1995).
Coffey et al., Reovirus therapy of tumors with activated ras pathway, Science, 282(5392):1332-1334 (1998).
Coukos et al., Multi-attenuated herpes simplex virus-1 mutant G207 exerts cytotoxicity against epithelial ovarian cancer but not normal mesothelium and is suitable for intraperitoneal oncolytic therapy, Cancer Gene Therapy, 7:275-83 (2000).
Cozzi et al., Xenotransplantation, where do we stand? Journal of Nephrology, 16:S16-S21 (2003).
Duggan et al., Predictive factors for long-term engraftment of autologous blood stem cells, Bone Marrow Transplant, 26(12):1299-1304 (2000).
Duman et al., Successful treatment of post-transplant Kaposi's sarcoma by reduction of immunosuppression, Nephrol. Dial. Transplant, 17:892-6 (2002).
Ezzat et al., An overview of breast cancer, Annals of Saudi Medicine, 17(1):10-15 (1997).
Freshney, Culture of animal cells: a manual of basic technique, second edition, p. 217 (1997).
Fueyo et al., A mutant oncolytic adenovirus targeting the Rb pathway produces anti-glioma effect in vivo, Oncogene, 19(1):2-12 (2000).
Gao et al., Rapid in situ hybridization technique for detecting malignant mouse cell contamination in human xenograft tissue from nude mice and in vitro cultures from such xenografts, Prostate, 39(1):67-70 (1999).
Garcia-Castro et al., Purging of leukemia-contaminated bone marrow grafts using suicide adenoviral vectors: an in vivo murine experimental model, Gene Therapy, 10:1328-1335 (2003).
Gariglio et al., Inhibition of interferon-gamma antiviral and antiproliferative activities by ras oncogene expression, Journal of the National Cancer Institute, 81:1014-1020 (1989).
Gentsch et al., Effect of neuraminidase treatment of cells and effect of soluble glycoproteins on type 3 reovirus attachment to murine L cells, J. Virol., 56(2):356-364 (1985).
Graham et al., Varying degrees of amplification of the N-ras oncogene in the human breast cancer cell line MCF-7, Cancer Research, 45:2201-2205 (1985).
Gulati et al., Rationale for purging in autologous stem cell transplantation, J. Hematother., 2(4):467-471 (1993).
Haig et al., The orf virus OV20.0L gene product is involved in interferon resistance and inhibits an interferon-inducible, double-stranded RNA-dependent kinase, Immunology, 93(3):355-340 (1998).
Hashiro et al., The preferential cytotoxicity of reovirus for certain transformed cell lines, Archives of Virology 54:307-315 (1977).
He et al., The gamma(1)34.5 protein of herpes simplex virus 1 complexes with protein phosphatase 1α to dephosphorylate the α subunit of the eukaryotic translation initiation factor 2 and preclude the shutoff of protein synthesis by double-stranded RNA-activated protein kinase, Proc. Nat. Acad. Sci., 94:843-848 (1997).
Hirai et al., Adenovirus p53 Purging for Human Breast Cancer Stem Cell Products, Acta Haematol., 101(2):97-105 (1999).
Janes et al., Activation of the Ras signaling pathway in human breast cancer cells overexpressing erbB-2, Oncogene, 9(12):3601-8 (1994).
Kawagishi-Kobayashi et al., Regulation of the protein kinase PKR by the vaccinia virus pseudosubstrate inhibitor K3L is dependent on residues conserved between the K3L protein and the PKR substrate eIF2α, Mol. Cell. Biology, 17 (7):4146-4158 (1997).
Kennedy et al., High-dose chemotherapy with reinfusion of purged autologous bone marrow following dose-intense induction as initial therapy for metastatic breast cancer, J. Natl. Cancer Inst., 83:920-6 (1991).
Kozma et al., The human c-kirsten ras gene is activated by a novel mutation in codon 13 in the breast carcinoma cell line MDA-MB231, Nucleic Acids Research, 15(15):5963-5971 (1987).
Lambright et al., Effect of pre-existing anti-herpes immunity on the efficacy of herpes simplex viral therapy in a murine intreperitoneal tumor model, Mol. Ther., 2(4):387-93 (2000).
Lichty et al., Abstract Identification of vesicular stomatitis virus as a leukemolytic agent, Blood, 96(11):213b (2000).
Lillo et al., Efficient and Nontoxic Adenoviral Purging Method for Autologous Transplantation in Breast Cancer Patients, Cancer Research, 62:5013-5018 (2002).
Lorence et al., Newcastle disease virus as an antineoplastic agent: induction of tumor necrosis factor-alpha and augmentation of its cytotoxicity, J. Natl. Cancer Inst., 80:1305-12 (1998).
Marini et al., Purging of contaminating breast cancer cells from hematopoietic stem cell grafts by adenoviral GAL-TEK gene therapy and magnetic antibody cell separation, Clin. Cancer Res., 5:1557-68 (1999).
Nemunaitis, Oncolytic viruses, Invest. New Drugs, 17(4):375-386 (1999).
Nielsen et al., P53 tumor suppressor gene therapy for cancer, Cancer Gene Ther., 5(1):52-63 (1998).
Nieto et al., Autologous stem-cell transplantation for solid tumors in adults, Hematol. Oncol. Clin. North Am., 13(5):939-968 (1999).
Nordon et al., Ex vivo manipulation of cell subsets for cell therapies, Artif Organs., 20(5):396-402 (1996).
Norman et al., Reovirus as a novel oncolytic agent, J. Clin. Invest., 105(8):1035-1038 (2000).
O'Reilly, Allogenic bone marrow transplantation: current status and future directions, J. of the American Society of Hematology, 62:941-64 (1983).
Paul et al., The anomeric form of sialic acid is the minimal receptor determinant recognized by reovirus, Virology, 172(1):382-385 (1989).
Rausch et al., Cooperation of p38 and extracellular signal-regulated kinase mitogen-activated protein kinase pathways during granulocyte colony-stimulating factor-induced hemopoietic cell proliferation, J. Biol. Chem., 274(7):4096-4105 (1999).
Reddy, Mobilization and collection of peripheral blood progenitor cells for transplantation, Transfus. Apher. Sci., 32(1):63-72 (2005).
Reichard et al., Newcastle disease virus selectively kills human tumor cells, J. of Surgical Research, 52(5):448-453 (1992).
Romano et al., Inhibition of double-stranded RNA-dependent protein kinase PKR by vaccinia virus E3: role of complex formation and the E3 N-terminal domain, Mol. Cell. Bio., 18(12):7304-7316 (1998).
Satoh et al., Involvement of ras p21 protein in signal-transduction pathways from interleukin 2, interleukin 3, and granulocyte/macrophage colony-stimulating factor, but not from interleukin 4, Proc. Natl. Acad. Sci. USA., 88(8):3314-3318 (1991).
Schpall et al., A prospective randomized trial of buffy coat versus CD34-selected autologous bone marrow support in high-risk breast cancer patients receiving high-dose chemotherapy, Blood, 90:4313-20 (1997).
Seth et al., Adenovirus-mediated gene transfer to human breast tumor cells: an approach for cancer gene therapy and bone marrow purging, Cancer Res., 56(6):1346-1351 (1996).

Sharp et al., The vaccinia virus E3L gene product interacts with both the regulatory and the substrate binding regions of PKR: implications for PKR autoregulation, Virol., 250(2):302-315 (1998).

Snyder et al., Posttransplant lymphoproliferative disorder following nonmyelopablative allogeneic stem cell transplantation, Am. J. Surg. Pathol., 28(6):794-800 (2002).

Spyridonidis et al., Minimal residual disease in autologous hematopoietic harvests from breast cancer patients, Ann. Oncol., 9(8):821-826 (1998).

Steele, Recent developments in the virus therapy of cancer, Proc. Soc. Exp. Biol. Med., 223(2):118-127 (2000).

Stewart et al., Superior autologous blood stem cell mobilization from dose-intensive cyclophosphamide, etoposide, cisplatin plus G-CSF than from less intensive chemotherapy regimens, Bone Marrow Transplant, 23(2):111-117 (1999).

Stodjl et al., Exploiting tumor-specific defects in the interferon pathway with a previously unknown oncolytic virus, Nature Medicine, 6(7):821-825 (2000).

Strong et al., Evidence that the epidermal growth factor receptor on host cells confers reovirus infection efficiency, Virology, 197(1):405-411 (1993).

Strong et al., The molecular basis of viral oncolysis: usurpation of the ras signaling pathway by reovirus, EMBO J., 17(12):3351-3362 (1998).

Strong et al., The v-erbB oncogene confers enhanced cellular susceptibility to reovirus infection, J. Virol., 70(1):612-616 (1996).

Sundaresan et al., Attenuated, replication-competent herpes simplex virus type 1 mutant G207: safety evaluation in mice, J. of Virology, 74:3832-41 (2000).

Thimmappaya et al., Adenovirus VAI RNA is required for efficient translation of viral mRNAs at late times after infection, Cell, 31:543-51 (1982).

Toda et al., Treatment of human breast cancer in a brain metastatic model by G207, a replication-competent multimutated herpes simplex virus 1, Human Gene Therapy, 9:2177-85 (1998).

Ueno et al., Allogeneic peripheral-blood progenitor-cell transplantation for poor-risk patients with metastatic breast cancer, J. Clin. Oncol., 16:986-993 (1998).

Van Weering et al., Ret receptor tyrosine kinase activates extracellular signal-regulated kinase 2 in SK-N-MC cells, Oncogene, 11:2007-2014 (1995).

Wantanabe et al., Autologous and allogeneic transplantation with peripheral blood CD34+ cells: a pediatric experience, Haematologica, 84:167-176 (1999).

Wiman, New p53-based anti-cancer therapeutic strategies, Med. Oncol., 15(4):222-228 (1998).

Winter, High-dose therapy with stem-cell transplantation in the malignant lymphomas. Oncology (Williston Park), 13(12):1635-1645 (1999).

Wu et al., Bone marrow purging by attenuated multi-mutated herpes simplex virus-1, Proc. Annu. Meet. AM Soc. Clin. Oncol., 16:91a, Abstract #319 (1997).

Wu et al., Bone marrow purging of neuroblastoma by attenuated multimutated herpes simplex virus, Proceedings of the American Association for Cancer Research Annual, 39:605 (1998).

Wu et al., Biological purging of breast cancer cells using an attenuated replication-competent herpes simplex virus in human hematopoietic stem cell transplantation, Cancer Res., 61(7):3009-3015 (2001).

Yazaki et al., Treatment of human malignant meningiomas by G207, a replication-competent multimutated herpes simplex virus 1, Cancer Research, 55:4752-6 (1995).

Yoon et al., An oncolytic herpes simplex virus type 1 selectively destroys diffuse liver metastases from colon carcinoma, FASEB J., 14(2):301-311 (2000).

Zachos et al., Expression of ras proto-oncogenes: regulation and implications in the development of human tumors, Critical Reviews in Oncology Hematology, 26:65-75 (1997).

Zorn et al., Induction of cytokines and cytotoxicity against tumor cells by Newcastle disease virus, Cancer Biotherapy, 9(3):225-235 (1994).

\* cited by examiner

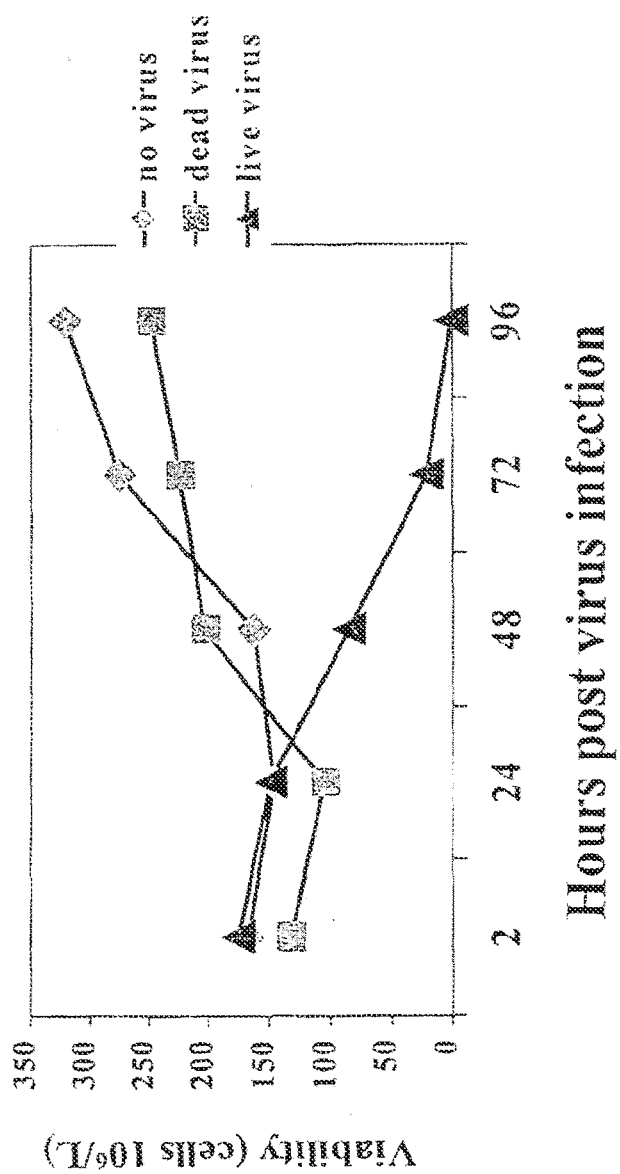

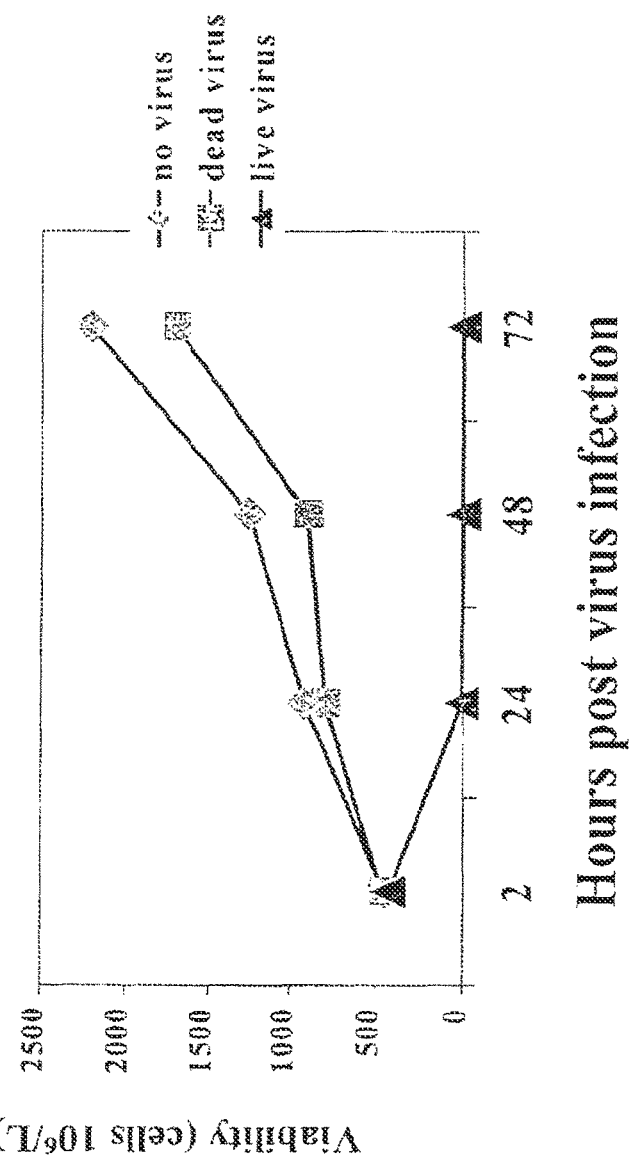

Effect of reovirus on MCF7 viability

REOVIRUS CLEARANCE OF RAS-MEDIATED NEOPLASTIC CELLS FROM MIXED CELLULAR COMPOSITIONS

RELATED INVENTIONS

This application is a continuation of U.S. patent application Ser. No. 12,726,002, filed Mar. 17, 2010, which is a divisional of U.S. patent application Ser. No. 11/807,930, filed May 30, 2007, now U.S. Pat. No. 7,725,534, which is a continuation of U.S. patent application Ser. No. 11/236,059, filed Sep. 26, 2005, now U.S. Pat. No. 7,431,932. U.S. patent application Ser. No. 11/236,059 is a continuation of U.S. patent application Ser. No. 09/847,356, filed May 3, 2001, now U.S. Pat. No. 6,994,858. U.S. patent application Ser. No. 09/847,356 claims the benefit of U.S. Provisional Applications Ser. No. 60/201,990, filed May 3, 2000, Ser. No. 60/205,389, filed May 19, 2000 and Ser. No. 60/268,054, filed Feb. 13, 2001 under 35 U.S.C. §119(e). The entire disclosure of each of the above provisional applications is hereby incorporated by reference.

FIELD OF THE INVENTION

The present invention relates to a method for removing ras-mediated neoplastic cells from mixed cellular compositions by infecting the mixed cellular compositions with reovirus which selectively lyse the ras-mediated neoplastic cells in the compositions.

REFERENCES

U.S. Pat. No. 6,136,307.
Armstrong, G. D. et al., "Studies on reovirus receptors of L cells: virus binding characteristics and comparison with reovirus receptors of erythrocytes", *Virology* 138:37: 37-48 (1984).
Bensinger, W. I., "Should we purge?", *Bone Marrow Tranplant.* 21:113-115 (1998).
Bos, J. L., "Ras Oncogenes in Human Cancer: A Review", *Canc. Res.* 49(17): 4682-4689 (1989).
Chandran and Niben, "Protease cleavage of reovirus capsid protein mu1 and mu1 C is blocked by alkyl sulfate detergents, yielding a new type of infectious subvirion particle", *J. of Virology.* 72(1):467-75 (1998).
Coffey, M. C. et al., "Reovirus therapy of tumors with activated Ras pathway", *Science* 282: 1332-1334 (1998).
Duggan, P. R., et al., "Predictive factors for long-term engraftment of autologous blood stem cells", *Bone Marrow Transplantation* 26(12): 1299-1304 (2000).
Fields, B. N. et al., Fundamental Virology 3rd Edition, Lippincott-Raven (1996).
Gao, J., B. Tombal and J. T. Isaacs, "Rapid in situ hybridization technique for detecting malignant mouse cell contamination in human xenograft tissue from nude mice and in vitro cultures from such xenografts", *Prostate* 39(1): 67-70, 1999.
Gentsch, J. R. K. and Pacitti, A. F., "Effect of neuraminidase treatment of cells and effect of soluable glycoproteins of type 3 reovirus attachment to murine L cells", *J. Virol.* 56:356: 356-64 (1985).
Neito, Y. and E. J. Shpall, "Autologous stem-cell transplantation for solid tumors in adults", *Hematol. Oncol. Clin. North Am.* 13(5): 939-968 (1999).
Norman, K. and P. Lee, "Reovirus as a novel oncolytic agent", *J. Clin. Invest.* 105 (8):1035-1038 (2000).
Paul R. W. et al., "*The alpha-anameric form of sialic acid is the minimal receptor determinant recognized by reovirus*", Virology 172: 382-385 (1989).
Sabin, A. B., *Science* 130: 966 (1959).
Spyridonidis, A. et al., "Minimal residual disease in autologous hematopoietic harvests from breast cancer patients", *Annals of Oncology* 9:821-826 (1998).
Stewart, D. A., et al., "Superior autologous blood stem cell mobilization from dose-intensive cyclophosphamide, etoposide, cisplatin plus G-CSF than from less intensive chemotherapy regimens", *Bone Marrow Transplant.* 23(2): 111-117 (1999).
Strong, J. E., et al., "The molecular basis of viral oncolysis: usurpation of the Ras signaling pathway by reovirus", *EMBO J.* 17: 3351-3362 (1998).
Strong, J. E. and P. W. Lee, "The v-erbV oncogene confers enhanced cellular susceptibility to reovirus infection", *J. Virol.* 70: 612-616 (1996).
Strong, J. E., et al., "Evidence (that the Epidermal Growth Factor on Host Cells Confers Reovirus Infection Efficiency", *Virology* 197(1): 405-411 (1993).
Winter, J. N., "High-dose therapy with stem-cell transplantation in the malignant lymphomas", *Oncology (Huntingt).* 13(12): 1635-1645 (1999).
WO 99/08692, published Feb. 25, 1999.

All of the above publications, patents and patent applications are herein incorporated by reference in their entirety to the same extent as if the disclosure of each individual publication, patent application or patent was specifically and individually indicated to be incorporated by reference in its entirety.

BACKGROUND OF THE INVENTION

Normally, cell proliferation is regulated by both growth-promoting signals and growth-constraining signals. These two kinds of signals for each cell would normally strike a balance in a manner which reflects the need of the body for the particular cell. If a cell fails to respond to the growth-constraining signals or over-responds to the growth-promoting signals, it will proliferate abnormally fast (referred to as neoplastic cells) and may eventually develop into cancer, a malignant neoplasm.

Chemotherapy, a current method of treating cancer, is generally based on the fast-proliferating property of cancer cells. Since cancer cells proliferate rapidly, they are more sensitive to drugs which inhibit cellular proliferation. In theory, by carefully choosing the dosage of chemotherapeutic drugs, one can inhibit cancer cell proliferation without seriously damaging normal cells. However, some normal cells, such as hematopoietic stem cells, also proliferate rapidly. Therefore, any dosage which is harmful to cancer cells is often also harmful to the hematopoietic stem cells. On the other hand, if the dosage is not high enough to kill the cancer cells, there is the risk that the cancer would reappear shortly after chemotherapy is terminated.

Because it is hard to find a dosage which selectively kills cancer cells, high-dose chemotherapy followed by autologous hematopoietic progenitor stem cell transplantation has gained extensive application as a therapeutic approach in many cancers (see, for example, Winter, 1999; Nieto and Shpall, 1999). In this approach, a portion of the hematopoietic stem cells is removed from a cancer patient, and the patient is then treated with high-dose chemotherapy which is lethal to rapid-proliferating cells, such as cancer cells and hematopoietic stem cells. Subsequently, the patient receives transplantation of autologous hematopoietic stem cells which have been previously removed from the same patient to regenerate the hematopoietic system.

A serious drawback of this therapy is that when the hematopoietic progenitor stem cells are removed from the patients, they are often contaminated with cancer cells. This is especially a problem when the patient has a cancer of the hematopoietic origin, but patients with a solid tumor may also suffer from contamination of the hematopoietic stem cells, particularly if the solid tumor has metastasized. As a result, when the removed cells are transplanted back to reestablish the hematopoietic system, some cancer cells may also be placed back to the cancer patient where they may proliferate again and contribute to cancer recurrence. It is therefore desirable to purge the autografts before transplantation.

Several methods have been employed to purge autographs (Spyridonidis et al., 1998; Bensinger 1998). The autograph can be treated with chemotherapy to kill the contaminating neoplastic cells in vitro. However, as discussed above, it is hard to find a dosage for the chemotherapeutic drug which selectively kills neoplastic cells or cancer cells but leaves normal hematopoietic stem cells intact. Autographs can also be treated with a toxin conjugated to antibodies which recognize an antigen that is specific to the neoplastic cells, but such a tumor specific antigen does not always exist.

It is also possible to separate stem cells from the other cells based on a stem cell specific surface marker (CD34) by using flow cytometry, affinity columns or magnetic beads. However, by selecting only certain hematopoietic cells, e.g., the CD34$^+$ cells, other hematopoietic cells such as T cells, B cells, monocytes and natural killer cells are also eliminated, and immune recovery may be delayed (Bensinger, 1998). This method also results in the loss of about half the CD34$^+$ cells and retention of some contaminating cancer cells (Spyridonidis et al., 1998). Therefore, there remains a need for a highly selective method with a reasonable yield to purge autografts which may contain neoplastic cells.

SUMMARY OF THE INVENTION

The present invention is directed to a method for removing ras-mediated neoplastic cells from mixed cellular compositions by infecting the mixed cellular compositions with reovirus which selectively lyses ras-mediated neoplastic cells. Since many neoplastic cells are associated with an activated ras pathway, the present invention can be used to remove the contaminating or spontaneous neoplastic cells from a wide variety of mixed cellular compositions.

Accordingly, one aspect of the present invention provides a method to remove ras-mediated neoplastic cells from a cellular composition suspected of containing such neoplastic cells, which method comprises contacting the cellular composition with reovirus under conditions which result in oncolysis of the ras-mediated neoplastic cells.

In a preferred embodiment of the present invention, a cellular composition comprising hematopoietic stem cells is treated to remove ras-mediated neoplastic cells which exist in the cellular composition as contaminating or spontaneously occurring neoplastic cells. Since reovirus is highly selective and lytically infects ras-mediated cells only, this method does not affect the ability of hematopoietic stem cells to differentiate and reconstitute the hematopoietic system. The method can be used to purge hematopoietic stem cells from bone marrow or blood. The hematopoietic stem cells may be autologous, allogeneic or xenogeneic.

In another embodiment of the invention, reovirus is used to remove ras-mediated neoplastic cells from a tissue or organ transplant prior to transplantation. Because this method can be applied without regard to the type or age of the transplant or of the ras-mediated cell, and because the reovirus is essentially harmless to normal cells and tissues, this method can be used as a routine practice to "clean up" any transplant before transplantation.

In another embodiment of the invention, reovirus can be used to treat cultured cell lines to remove cells which are spontaneously transformed due to activation of the ras pathway. This method can also be used to treat semen or donor eggs before artificial insemination or other reproduction-related procedures.

The reovirus useful in this invention may be any reovirus. Preferably the reovirus is a mammalian reovirus, more preferably a human reovirus. Still more preferably the reovirus is a serotype 3 reovirus, most preferably the Dearing Strain reovirus.

In another embodiment of the invention, the method further comprises the step of freezing and storing the reovirus-treated cellular composition in a solution containing DMSO. DMSO is routinely used to freeze and store animal cells but it denatures the reovirus. Therefore this treatment removes infectious reovirus from the cellular composition while preserving the activity of the composition in the frozen state for a prolonged period of time.

In another embodiment of the present invention, reovirus is removed from the reovirus-treated cellular composition by subjecting the mixture to anti-reovirus antibodies or a combination of anti-reovirus antibodies and complement in order to lyse the reovirus. Alternatively or additionally, anti-reovirus antibodies which recognize a molecule on the surface of the reovirus particle may be used to remove the reovirus particles by immobilizing the antibodies, applying the cellular composition to the immobilized antibodies, and collecting the part of the composition which does not bind to the antibodies.

Similarly, anti-reovirus antibodies can be administered to the transplant recipient to eliminate reovirus in vivo, or the recipient can be given an immune system stimulant to achieve this purpose.

In another embodiment of the present invention, reovirus is removed from the reovirus-treated cellular composition by using a gradient which can separate reovirus from cells.

Also provided are cellular compositions which have been treated with reovirus to remove ras-mediated neoplastic cells. Such compositions may be used for in vitro research, or in transplantation, insemination, or other in vivo procedures. The transplantation may be autologous, allogeneic, or even xenogeneic. Preferably the transplantation is autologous. More preferably, the composition comprises hematopoietic stem cells.

BRIEF DESCRIPTION OF THE DRAWINGS

FIG. 1

FIGS. 1A-1C show the number of viable cells in MCF7 (FIG. 1A), SKBR3 (FIG. 1B) or MDA MB 468 (ATCC No. HTB132; FIG. 1C) which were infected with live reovirus, dead virus or no virus as indicated.

FIG. 2

FIG. 2 shows that apoptosis was induced by reovirus infection in MCF7, SKBR3 or MDA MB 468 cells.

FIG. 3

FIG. 4

DETAILED DESCRIPTION OF THE INVENTION

Figure 1A:
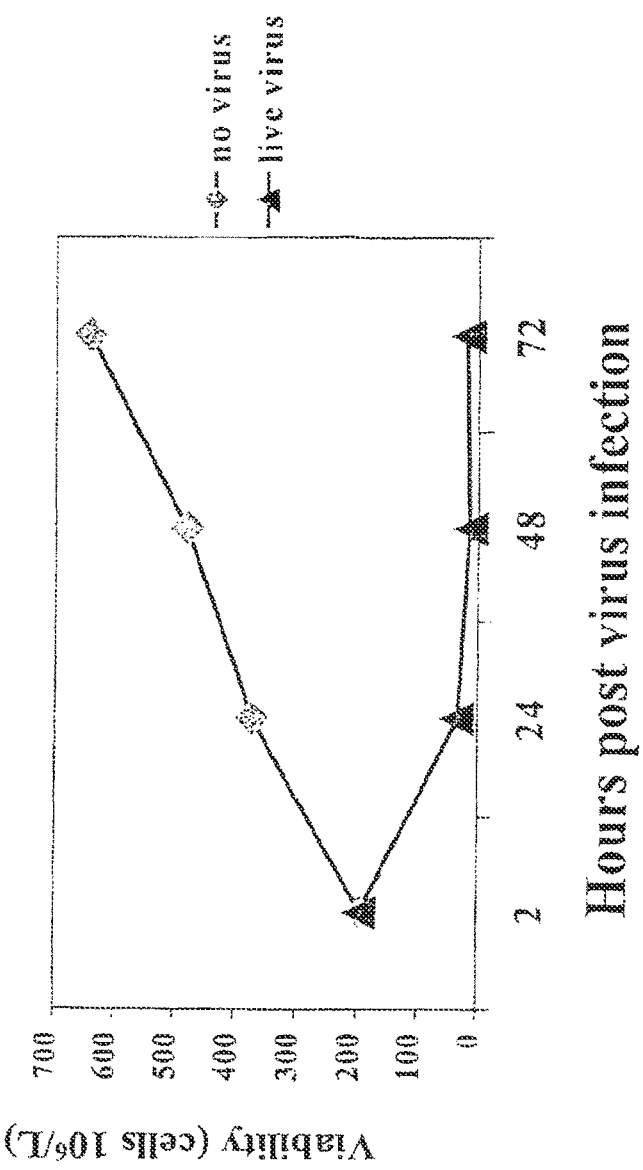
Figure 1D:
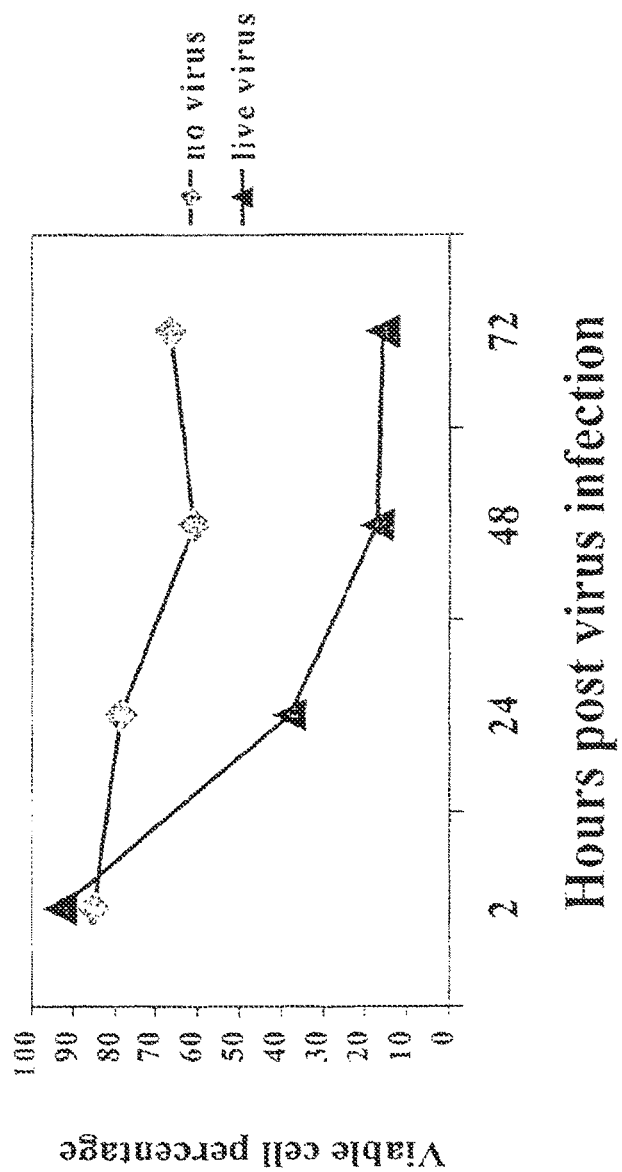
FIG. 1D shows the percentage of MCF7 cells which were viable at various time points after reovirus infection.
Figure 2A:
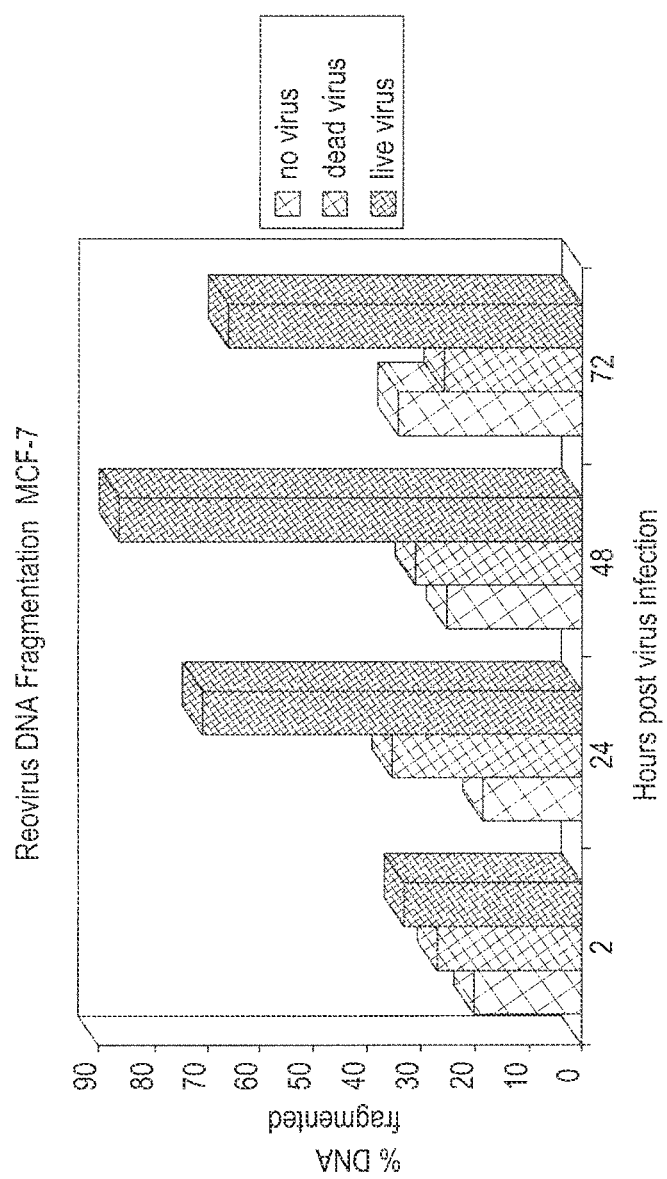
FIGS. 2A-2C demonstrate the percentage DNA which were fragmented after reovirus infection.
Figure 2B:
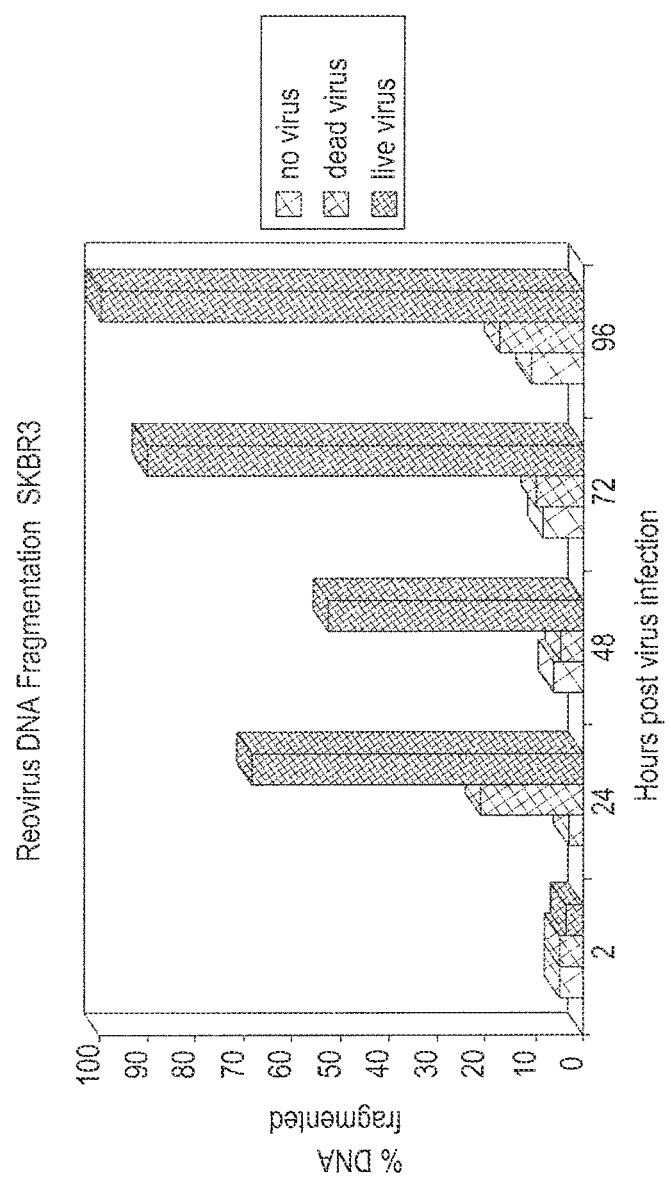
Figure 2C:
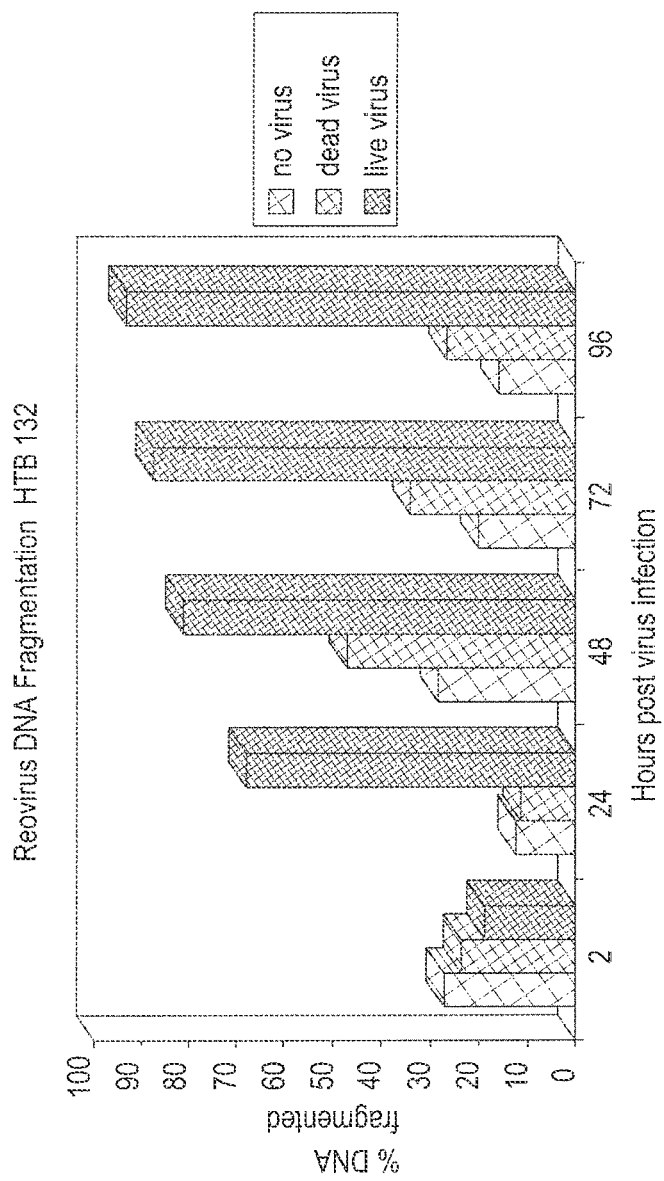
Figure 2D:
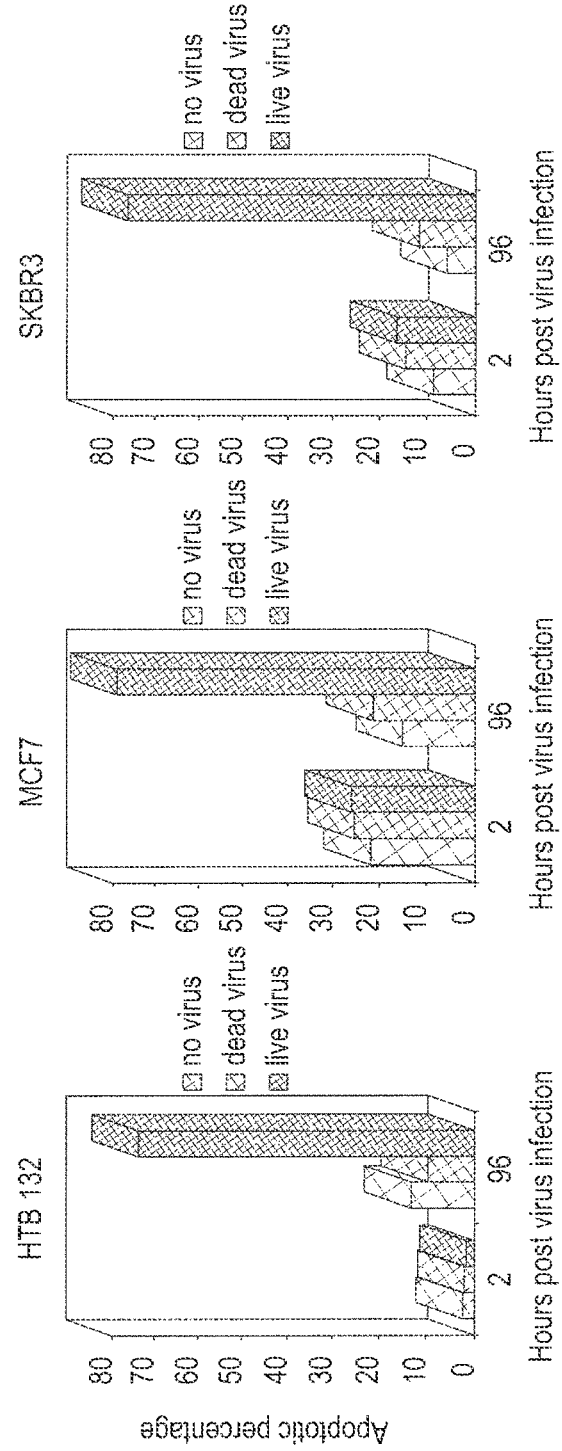
FIG. 2D shows the percentage of the apoptotic marker Annexin V staining after reovirus infection.
Figure 2E:
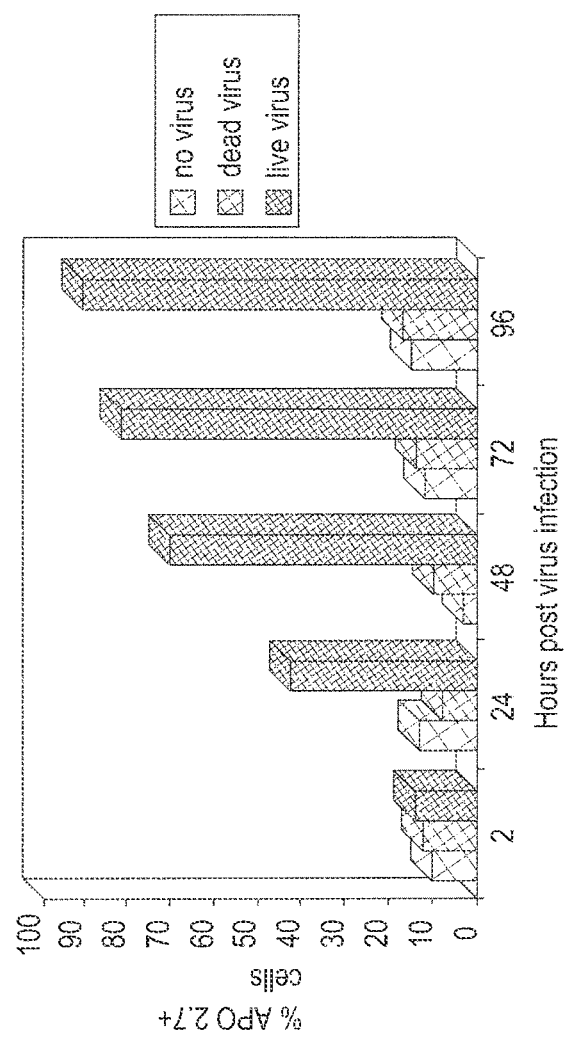
FIGS. 2E-2G show the percentage of APO2.7+ cells in each cell type as indicated.
Figure 2F:
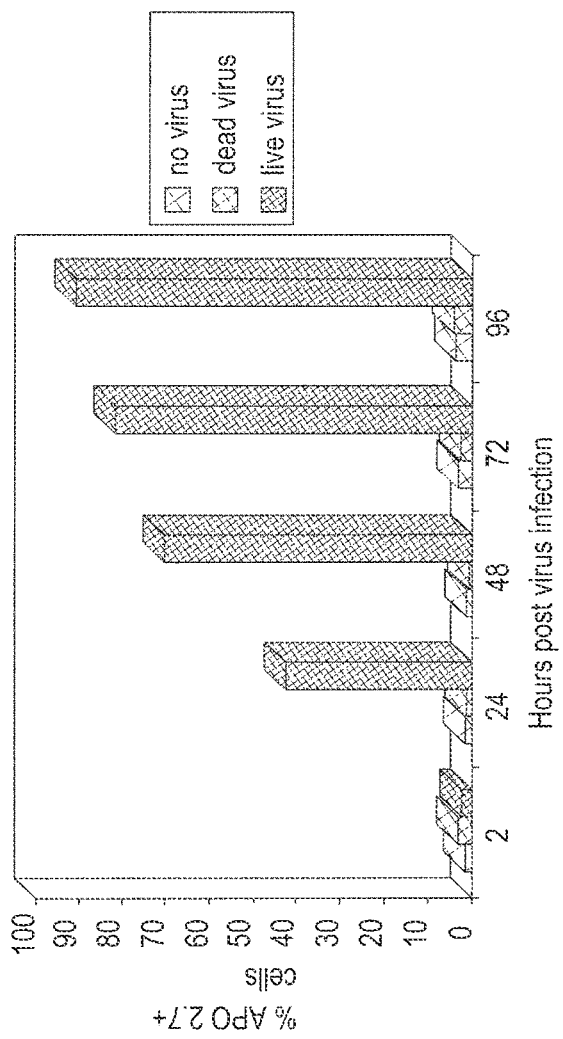
Figure 2G:
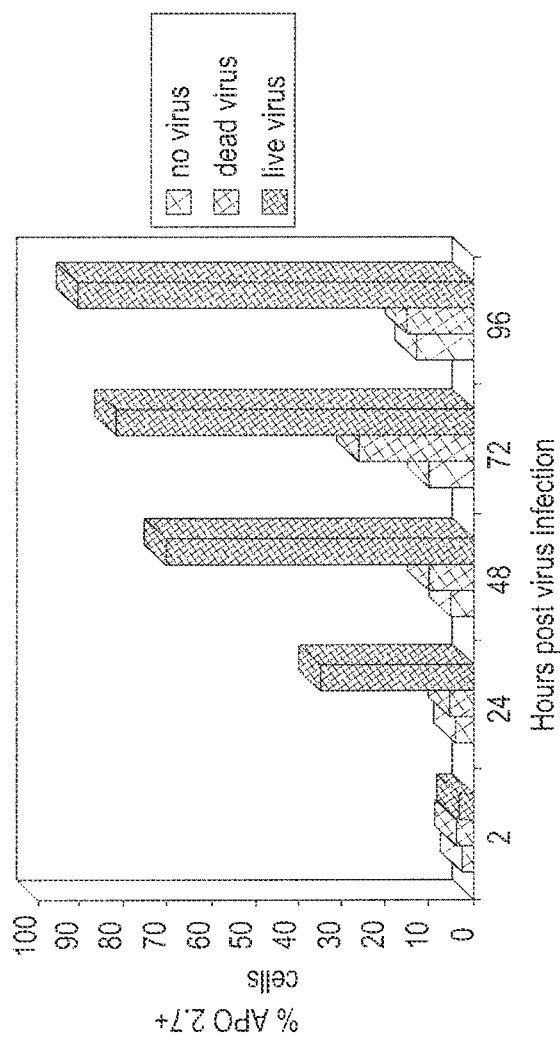

The invention is directed to methods of removing ras-mediated neoplastic cells from a cellular composition by using reovirus, and to compositions which have been treated according to these methods.

Prior to describing the invention in further detail, the terms used in this description are defined as follows unless otherwise indicated.

Definitions

As used herein, "neoplastic cells", also known as "cells with a proliferative disorder", refer to cells which proliferate without the normal growth inhibition properties. A new growth comprising neoplastic cells is a neoplasm or tumor. A neoplasm is an abnormal tissue growth, generally forming a distinct mass, that grows by cellular proliferation more rapidly than normal tissue growth. Neoplasms may show partial or total lack of structural organization and functional coordination with normal tissue. As used herein, a neoplasm is intended to encompass hematopoietic neoplasms as well as solid neoplasms.

A neoplasm may be benign (benign rumor) or malignant (malignant tumor or cancer). Malignant tumors can be broadly classified into three major types. Malignant neoplasms arising from epithelial structures are called carcinomas, malignant neoplasms that originate from connective tissues such as muscle, cartilage, fat or bone are called sarcomas and malignant tumors affecting hematopoietic structures (structures pertaining to the formation of blood cells) including components of the immune system, are called leukemias and lymphomas. Other neoplasms include, but are not limited to neurofibromatosis.

As used herein, "ras-activated neoplastic cells" or "ras-mediated neoplastic cells" refer to cells which proliferate at an abnormally high rate due to, at least in part, activation of the ras pathway. The ras pathway may be activated by way of ras gene structural mutation, elevated level of ras gene expression, elevated stability of the ras gene message, or any mutation or other mechanism which leads to the activation of ras or a factor or factors downstream or upstream from ras in the ras pathway, thereby increasing the ras pathway activity. For example, activation of EGF receptor, PDGF receptor or Sos results in activation of the ras pathway. Ras-mediated neoplastic cells include, but are not limited to, ras-mediated cancer cells, which are cells proliferating in a malignant manner due to activation of the ras pathway.

As used herein, "cellular composition" means a composition comprising cells. The composition may contain non-cellular matter. For example, whole blood is a cellular composition which contains plasma, platelets, hormones and other non-cellular matter in addition to cells such as erythrocytes and leukocytes. A cellular composition may contain cells of various types, origin or organization. For example, tissues and organs which contain different cell types arranged in defined structures are considered cellular compositions.

As used herein, "reovirus" refers to any virus classified in the reovirus genus. The name reovirus (Respiratory and enteric orphan virus) is a descriptive acronym suggesting that these viruses, although not associated with any known disease state in humans, can be isolated from both the respiratory and enteric tracts (Sabin, 1959). The term "reovirus" refers to all viruses classified in the reovirus genus.

The human reovirus consists of three serotypes: type 1 (strain Lang or T1L), type 2 (strain Jones, T2J) and type 3 (strain Dearing or strain Abney, T3D). The three serotypes are easily identifiable on the basis of neutralization and hemagglutinin-inhibition assays (See, for example, Fields et al., 1996).

The reovirus may be naturally occurring or modified. The reovirus is "naturally-occurring" when it can be isolated from a source in nature and has not been intentionally modified by humans in the laboratory. For example, the reovirus can be from a "field source", that is, from a human who has been infected with the reovirus.

The reovirus may be modified but still capable of lytically infecting a mammalian cell having all active ras pathway. The reovirus may be chemically or biochemically pretreated (e.g., by treatment with a protease, such as chymotrypsin or trypsin) prior to administration to the proliferating cells. Pretreatment with a protease removes the outer coat or capsid of the virus and may increase the infectivity of the virus. The reovirus may be coated in a liposome or micelle (Chandron and Nibert, 1998) to reduce or prevent an immune response from a mammal which has developed immunity to the reovirus. For example, the virion may be treated with chymotrypsin in the presence of micelle forming concentrations of alkyl sulfate detergents to generate a new infectious subvirion particle.

The reovirus may be a recombinant reovirus from two or more types of reoviruses with differing pathogenic phenotypes such that it contains different antigenic determinants, thereby reducing or preventing an immune response by a mammal previously exposed to a reovirus subtype. Such recombinant virions can be generated by co-infection of mammalian cells with different subtypes of reovirus with the resulting resorting and incorporation of different subtype coat proteins into the resulting virion capsids.

"Resistance" of cells to reovirus infection indicates that infection of the cells with the virus did not result in significant viral production or yield. Cells that are "susceptible" are those that demonstrate induction of cytopathic effects, viral protein synthesis, and/or virus production. Resistance to reovirus infection was found to be at the level of gene translation, rather than at early transcription: while viral transcripts were produced, virus proteins were not expressed. Without being limited to a theory, it is thought viral gene transcription in resistant cells correlated with phosphorylation of an approximately 65 kDa cell protein, determined to be double-stranded RNA-activated protein kinase (PKR);

that was not observed in transformed cells. Phosphorylation of PKR lead to inhibition of translation. When phosphorylation was suppressed by 2-aminopurine, a known inhibitor of PKR, drastic enhancement of reovirus protein synthesis occurred in the untransformed cells.

As used herein, "oncolysis" or "decrease of viability of neoplastic cells" refers to a decrease of at least about 20% in viability of the target neoplastic cells. The viability can be determined by a viable cell count of the treated cells, and the extent of decrease can be determined by comparing the number of viable cells in the treated cells to that in the untreated cells, or by comparing the viable cell count before and after reovirus treatment. The decrease in viability is preferably at least about 50%, more preferably at least about 70%, still more preferably at least about 80%, and most preferably at least about 90%.

As used herein, a "transplant recipient" is a mammal which receives a transplantation of cellular compositions. Preferably the recipient is a human, and more preferably a recipient is a human who is receiving transplantation in the treatment of cancer.

As used herein, "CPE" as an apoptotic marker refers to the cytopathic effects typically associated with apoptosis which are observable under the microscope, such as cell membrane blebbing, nuclear condensation and chromatin condensation.

Methods

The present invention relates to the use of reovirus to remove ras-mediated neoplastic cells from cellular compositions which are suspected of containing such neoplastic cells. Since the activated ras pathway is associated with many tumors, this, invention can be applied to cellular compositions suspected of having any of a large variety of neoplastic cells.

For mammalian reoviruses, the cell surface recognition signal is sialic acid (Armstrong, 1984; Gentsch and Pacitti, 1985; Paul et al., 1989). Due to the ubiquitous nature of sialic acid, reovirus binds efficiently to a multitude of cell lines and as such can potentially target many different tissues; however, there are significant differences in susceptibility to reovirus infection between cell lines. One reason for this discrepancy in susceptibility may be the activity of the ras pathway in each cell type.

We recently discovered that reovirus selectively lyses ras activated neoplastic cells in vitro, in vivo and ex vivo (Coffey et al. 1998; WO 99/08692). Normally, cells are not susceptible to reovirus infection. However, when the ras pathway is activated, reovirus can successfully replicate in the cells and eventually results in lysis of the host cells. For example, when reovirus-resistant NIH 3T3 cells were transformed with activated Ras or Sos, a protein which activates Ras, reovirus infection was enhanced (Strong et al., 1998). Similarly, mouse fibroblasts that are resistant to reovirus infection became susceptible after transfection with the EGF receptor gene or the v-erbB oncogene (Strong et al., 1993; Strong et al., 1996).

Without being limited to a theory, it seems that reovirus replication is regulated at the translational level (Strong et al., 1998; Norman et al., 2000). In untransformed NIH 3T3 cells, early viral transcripts activate the double-stranded RNA-activated protein kinase (PKR), which inhibits translation, thereby inhibiting viral replication. Activated Ras (or an activated element of the ras pathway) presumably inhibits or reverses PKR activation. Therefore, viral protein synthesis proceeds, viral particles are made, and the cells are eventually lysed.

The ras oncogene accounts for a large number of tumors. Activating mutations of the ras gene itself occur in about 30% of all human tumors (Bos, J. L., 1989), primarily in pancreatic (90%), sporadic colorectal (50%) and lung (40%) carcinomas, and myeloid leukemia (30%). Activation of the factors upstream or downstream of ras in the ras pathway is also associated with tumors. For example, overexpression of HER2/Neu/ErbB2 or the epidermal growth factor (EGF) receptor is common in breast cancer (25-30%), and overexpression of platelet-derived growth factor (PDGF) receptor or EGF receptor is prevalent in gliomas and glioblastomas (40-50%). EGF receptor and PDGF receptor are both known to activate ras upon binding to their respective ligand, and v-erbB encodes a constitutively activated receptor lacking the extracellular domain.

We demonstrate in this invention that reovirus efficiently caused oncolysis of three breast cancer model systems, MCF7, SKBR3 and MDA MB 468, by inducing apoptosis in the infected cells (Example 1). Thus, reovirus treatment resulted in a marked decrease in viability of MCF7, SKBR3 and MDA MB 468 cells, while controls treated with no virus or dead virus grew normally (FIGS. 1A-1D). The decrease in viability was accompanied by characteristics which are associated with apoptosis, such as DNA fragmentation, annexin V or APO 2.7 staining positivity (FIGS. 2A-2G) and cytopathic effects, such as cell membrane blebbing, nuclear condensation and chromatin condensation observed under the microscope.

Figure 3A:
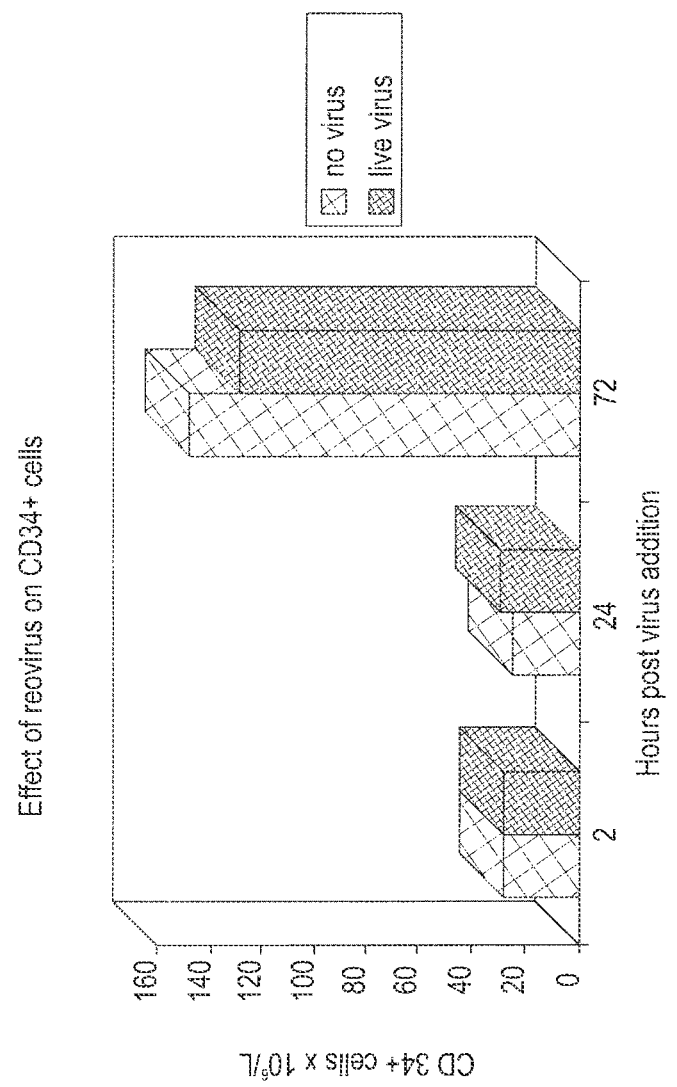
FIG. 3A shows the number of viable cells at various time points after CD34+ stem cells had been infected with reovirus.

Since reovirus infection is usually blocked at the translational level in normal cells but not in ras-mediated neoplastic cells, we examined the extent of protein synthesis in reovirus treated MCF7 cells and $CD34^+$ stem cells (Example 2). Indeed, viral proteins were synthesized in the reovirus infected cancer cell line, but not in $CD34^+$ stem cells which were also treated with reovirus (data not shown). This result suggests that it will be safe to treat hematopoietic stem cells with reovirus, since reoviral proteins were not synthesized in reovirus treated stem cells and cellular protein synthesis proceeded normally. To confirm this point, viability of the reovirus treated $CD34^+$ cells was determined at various time points after reovirus treatment (Example 3). Cell numbers in population treated with live reovirus or no virus were similar after each time point (FIG. 3A), indicating that $CD34^+$ cells are not susceptible to reovirus infection.

Figure 3B:
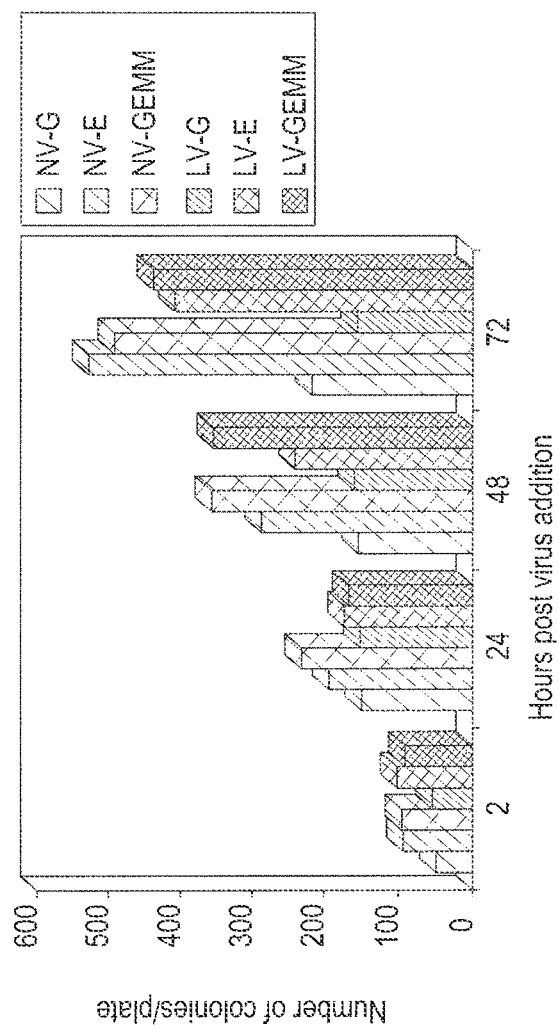
FIG. 3B shows the effect of reovirus on long-term stem cell culture. Stem cells were infected with reovirus and incubated for 2, 24, 48 or 72 hours, respectively, then the cells were diluted and cultured for 14 days to allow individual colonies to form. The number of each kind of colony, granulocytes (G), erythroids (E) or granulocyte erythroid macrophage megakaryocyte (GEMM), was then determined for cells infected with no virus (NV) or live virus (LV), respectively. For example, NV-G stands for the granulocyte colonies derived from cells which were treated with no virus, and LV-G stands for those derived from cells which were treated with live reovirus.

In order for reovirus to be useful in purging hematopoietic stem cell in high dose chemotherapy treatments, it is essential that the reovirus treatment does not alter the ability of stem cells to differentiate into each and every hematopoietic lineage to reconstitute the whole hematopoietic system. Therefore, long term effect of reovirus treatment was assessed (Example 3). $CD34^+$ cells treated with either no virus or live virus showed essentially no difference in their ability to differentiate into granulocytes, erythroids, or granulocyte erythroid macrophage megakaryocytes even after 72 hours of reovirus treatment (FIG. 3B). The ratio between these three lineages also remained the same after this prolonged treatment. Accordingly, reovirus treatment neither killed $CD34^+$ cells nor changed the potential of them to reconstitute the hematopoietic system.

Furthermore, reovirus is capable of purging a mixed cellular composition, as demonstrated by the selective killing of MCF7, SKBR3 or MDA MB 468 cells in a mixture of cancer cells and apheresis product which contained $CD34^+$ stem cells (Example 4). By measuring CD34 and cytokeratin, a marker specific for epithelial cells such as MCF7, SKBR3 or MDA MB 468, it was shown that reovirus essentially eliminated the cancer cells from the mixed cellular composition (FIGS. 4A-4C) while leaving the stem cells intact. Therefore, reovirus treatment is an efficient method to purge neoplastic cells from hematopoietic stem cell compositions.

Accordingly, in the preferred embodiment of this invention, stem cell-containing autographs are treated with reovirus prior to transplantation to remove the contaminating or spontaneous ras-mediated neoplastic cells. This increases the efficacy of the high dose chemotherapy/autologous hematopoietic stem cell transplantation treatment. Of particular interest will be the treatment of Hodgkin's disease, multiple myeloma, non-Hodgkin's lymphoma, acute myelogenous leukemia, germ cell (testicular) cancers, brain tumors, and breast tumors, since high dose chemotherapy and autologous stem cell transplantation have been performed efficiently in patients with these tumors. However, it is contemplated that the present method will be useful in other cancers as well to remove any ras-mediated neoplastic cells, since activation of the ras pathway may occur in any cell or tissue type.

Hematopoietic progenitor stem cells can be removed from bone marrow of the patient in advance of treatment. Alternatively, in a cancer patient who has been receiving traditional, non-high dose chemotherapy, many stem cells typically appear in the peripheral blood. Therefore, hematopoietic progenitor stem cell can be removed from the blood as apheresis product, which can be stored for a long time before being transplanted. The present invention can be applied to stem cell-containing autographs which are harvested from any tissue source, including bone marrow and blood.

Although reovirus normally is not associated with any known disease, it may be more infectious to cancer patients whose immune systems are weakened due to chemotherapy. Accordingly, in another embodiment of this invention, the stem cell compositions which have been treated with reovirus are frozen in a solution containing DMSO and thawed prior to transplantation. While DMSO is routinely used to freeze and store animal cells, it denatures reovirus, thereby removing infectious reovirus from the stem cell preparation. This reduces the risk that reovirus may cause undesired infections when it is introduced into the transplant recipient via stem cell transplantation.

In another embodiment, the reovirus-treated cell compositions are treated with anti-reovirus antibodies or a combination of anti-reovirus antibodies and complements in order to inactivate or lyse the reovirus. Alternatively or additionally, anti-reovirus antibodies which recognize a molecule on the surface of the reovirus particle may be used to remove the reovirus particles from the reovirus-treated cellular composition. Thus, the antibodies are immobilized to a column, beads or any other material or device known in the art, the cellular composition is applied to the immobilized antibodies, and the part of the composition which does not bind to the antibodies is collected according to a procedure suitable for the particular method of immobilization.

Another method which may be used to remove reovirus from the reovirus-treated mixture is to subject the mixture to a gradient which separates cells from the virus, and collect the layer that contains only the cells.

In another embodiment, the transplant recipient is given treatments to stimulate the immune system in order to reduce the risk of reovirus infection. This treatment may be performed prior to, contemporaneously with, or after the transplantation, but is preferably performed prior to the transplantation. As an alternative treatment or in conjunction with the immune system stimulant, the recipient can be given anti-reovirus antibodies in order to reduce the risk of reovirus infection.

In addition to hematopoietic stem cells, the present invention can be broadly applied to remove ras-mediated neoplastic cells from many other cellular compositions. For example, reovirus can be used as a routine practice to "clean up" (remove ras-mediated neoplastic cells from) any tissue or organ transplant. Application of the present invention is not limited by cell or tissue type because as discussed above, the receptor for reovirus is ubiquitous, and the mechanism in normal cells to inhibit reovirus replication, PKR, is also ubiquitous. Therefore, any cell may become a ras-mediated neoplastic cell and become susceptible to reovirus infection. Of particular interest will be the use of the claimed methods to clean up whole blood or any portion thereof for a subsequent transfusion. Similarly, tissue or organ transplantation has become increasingly common, and it will be beneficial if the transplant can be treated to remove ras-mediated neoplastic cells before transplantation. Liver, kidney, heart. cornea, skin graft, pancreatic islet cells, bone marrow or any portions thereof are just a few examples of the tissues or organs to which this invention can be applied.

The tissue or organ can be autologous, allogeneic or xenogeneic. The tissue or organ may also be derived from a transgenic animal, be a tissue/organ which is developed in vitro from stem cells, or be expanded ex vivo. The tissue or organ to be treated with reovirus can be from an embryonic or adult origin. For example, embryonic neuronal cells can be treated before being transplanted into an Alzheimer's patient. Similarly, the invention can be used to treat semen or donor eggs ex vivo.

Application of the present invention is not limited to transplants. Rather, any cellular compositions can be "cleaned up" with reovirus for any purpose. Thus, all the examples described above are applicable even if the tissue or organ is not meant for transplantation.

Cell lines may also be treated routinely to safeguard against spontaneous or contaminating ras-mediated neoplastic cells. Again, any cell line will be a good candidate for this method except, of course, a cell line transformed by means of activation of the ras pathway.

Recently, many laboratories have been attempting to establish serially transplantable xenografts of human prostate cancer tissue inoculated into immune-compromised mice. However, contamination with mouse cancer cells often occurs during the serial passage of the xenografts and these calls can eventually outgrow the human prostate cancer cells (Gao et al., 1999). The present invention will be a simple solution to this problem if the contaminating cancer is ras-mediated and the xenograft is not.

The following examples are offered to illustrate this invention and are not to be construed in any way as limiting the scope of the present invention.

EXAMPLES

In the examples below, the following abbreviations have the following meanings Abbreviations not defined have their generally accepted meanings
μM=micromolar
mM=millimolar
M=molar
ml=milliliter
μl=microliter
mg=milligram
μg=microgram
PAGE=polyacrylamide gel electrophoresis
rpm=revolutions per minute
FBS=fetal bovine serum DIT=dithiothrietol
SDS=sodium dodecyl sulfate
PBS=phosphate buffered saline
DMEM=Dulbecco's modified Eagle's medium
α-MEM=α-modified Eagle's medium
β-ME=β-mercaptoethanol
MOI=multiplicity of infection
PFU=plaque forming units
PKR=double-stranded RNA activated protein kinase
EGF=epidermal growth factor
PDGF=platelet derived growth factor
DMSO=dimethylsulfoxide
CPE=cytopathic effect Example 1

Reovirus Induced Oncolysis and Apoptosis in Breast Cancer Cells

To determine the effect of reovirus on the viability of neoplastic cells, we first used three breast cancer model systems, MCF7 (ATCC number HTB-22), SKBR3 (ATCC number HTB-30) and MDA MB 468 (ATCC number HTB 132). Cells of each cell line were grown to 50-60% confluency and infected with reovirus serotype 3, strain Dearing, at a multiplicity of infection of 40. Reovirus was obtained and maintained as described in U.S. Pat. No. 6,136,307. Reovirus infected and non-infected cells were harvested at 0, 24, 48 and 72 hours after infection and the viability was determined.

The results are shown in FIGS. 1A-1D. Viable cell count in reovirus-infected MCF7 (FIG. 1A), SKBR3 (FIG. 1B) or MDA MB 468 cells (FIG. 1C) dropped significantly after the infection, while the cells infected with dead virus or no virus proliferated as expected. Reovirus treatment caused MCF7 (FIG. 1D) and SKBR3 viability to drop from 93% to 16% by 72 hours after infection. In MDA MB 468 cells, virus treated intact cell numbers dropped to 12.7%, 8.8% and 3.6% of the original cell counts, respectively, at 24, 48 and 72 hours after infection. Thus, reovirus caused oncolysis efficiently in all three kinds of cancer cells.

The cells died by apoptosis. Typical apoptotic markers such as CPE, Annexin-V and DNA laddering could be observed in a time course parallel to the decrease of viability. FIGS. 2A-2G show the percentage of DNA fragmentation (2A-2C), Annexin V staining (2D) or AP02. 7+ cells (2E-2G) at various time points after reovirus infection. The reovirus treated cells exhibited all signs of apoptosis at a dramatic level compared to the no virus or dead virus controls, demonstrating that reovirus induced apoptosis in all of these three cell lines. Apoptosis in the controls seemed to increase slowly with time as well, probably because cells began to die when they had grown too densely.

Example 2

Reovirus Selectively Inhibited Protein Synthesis in Cancer Cells but not CD34+ Stem Cells For further proof of selective viral infection of cancer cells, $^{35}$S labeling/SDS/PAGE of viral proteins was undertaken. Viral protein synthesis was evident after 1-2 days in MCF7 cells infected, with reovirus, while cellular protein synthesis decreased at the same time, indicating that reovirus had taken over the cellular machinery. At 4 days after infection, no protein synthesis could be detected anymore, suggesting that all the cells had been killed. In the control experiments, where cells were infected with dead reovirus or no virus, there was no viral protein synthesis, whereas cellular protein synthesis was at the normal level. In contrast, $^{35}$S labeling of CD34+ stem cells in the presence or absence of reovirus showed no viral protein synthesis up to 72 hours after the addition of virus. Therefore, reovirus selectively infect MCF7 cells but not CD34+ stem cells.

Example 3

Reovirus Treatment Neither Inhibited Cell Proliferation nor Altered Differentiation Potential of CD34+ Cells Consistent with the protein synthesis results, viable cell count indicated that reovirus treatment did not decrease the number of viable cells in CD34+ cells (FIG. 3A) as compared to the no virus control.

While the number of CD34+ cells was unaffected by reovirus infection, there remained the question whether reovirus changed the potential of CD34+ stem cells to differentiate into all the hematopoietic lineages in the appropriate proportion. If this was the case, reovirus treated stem cells would not be a good candidate for the reconstitution of the whole hematopoietic system. To investigate this possibility, CD34+ cells were incubated with reovirus for 2, 24, 48 or 72 hours, respectively. The reovirus was then removed and the cells were diluted and cultured in fresh media for 14 days to allow colonies to form. Each colony was examined to determine if it belongs to the granulocyte, erythroid, or granulocyte erythroid macrophage megakaryocyte lineage. As shown in FIG. 3B, stem cells treated with live virus (LV) yielded similar numbers of granulocytes (G), erythrocytes (E) or granulocyte erythroid macrophage megakaryocytes (GEMM) as the no virus (NV) control. Therefore, reovirus treatment did not change the differentiation potential of CD34+ cells.

Example 4

Reovirus Selectively Removed Cancer Cells from a Mixed Cellular Composition

Figure 4A:
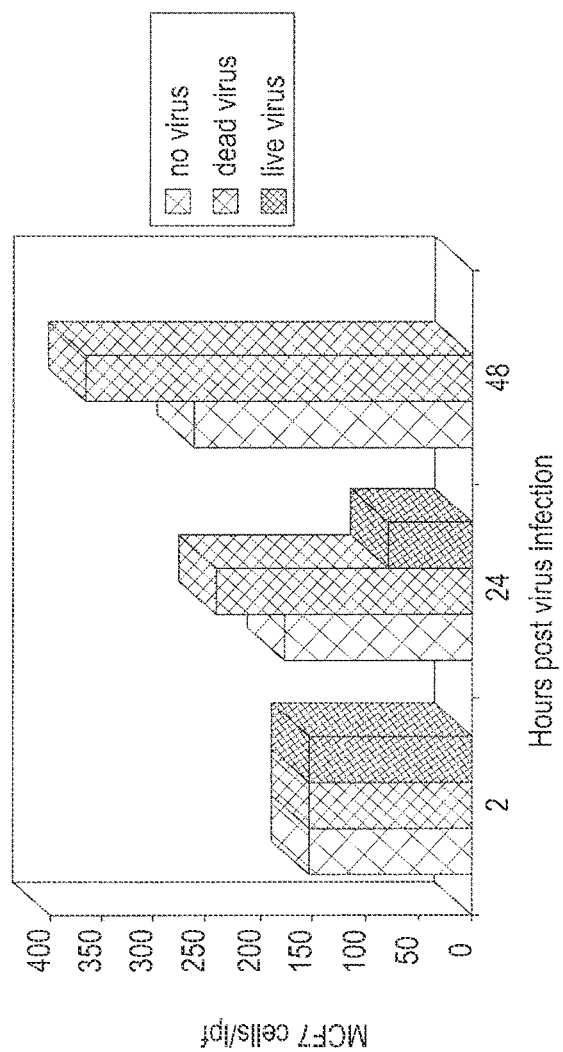
FIGS. 4A-4C show the purging effects of reovirus on -mixtures of apheresis product with MCF7, HTB-132 or SKBR3 cells, respectively.
Figure 4B:
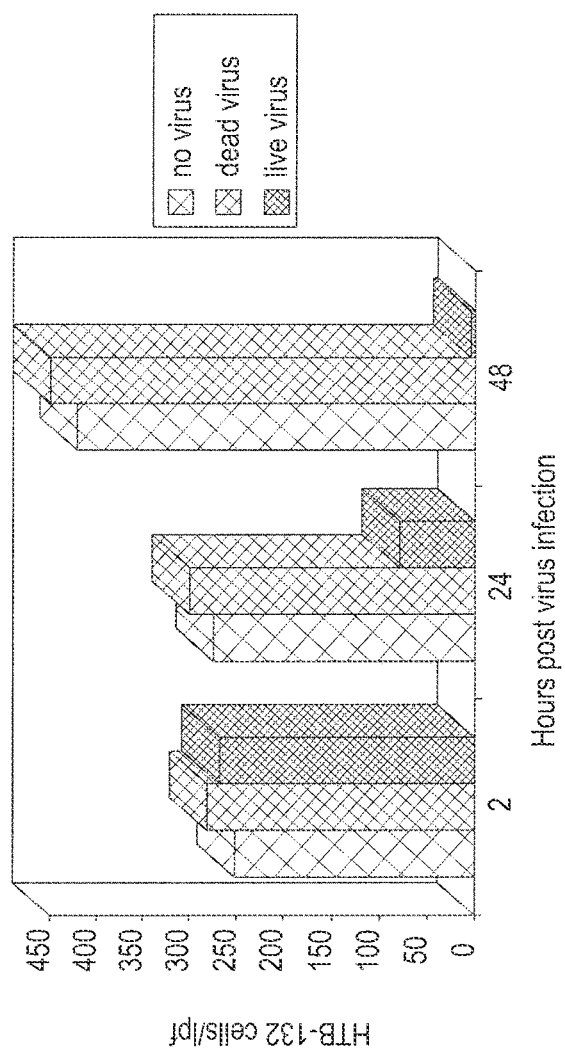
Figure 4C:
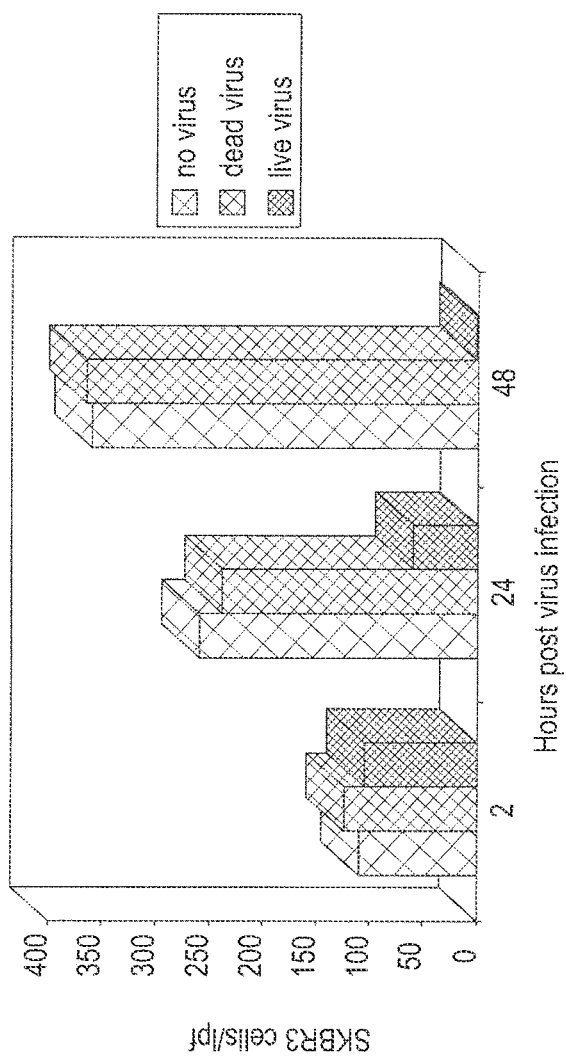

Neoplastic cells were mixed with apheresis product and subjected to reovirus infection to investigate if reovirus can selectively remove neoplastic cells from the mixed cellular composition. Apheresis product was prepared according to a procedure previously described (Stewart et al., 1999; Duggan et al., 2000). When admixtures of apheresis product (90%) and MCF7 (10%) were treated with reovirus and tested daily for cell count and viability, there was a 100-fold depletion in the numbers of cytokeratin-positive MCF7 cells while the CD34+ stem cells remained intact and viable (FIG. 4A). Reovirus was similarly effective in selectively removing MDA MB 468 (FIG. 4B) or SKBR3 cells (FIG. 4C) from their mixture with apheresis product, respectively. These results demonstrate that reovirus can selectively kill neoplastic cells in a cell mixture and leave the stem cells intact.

We claim:

1. A cellular composition for transplantation, wherein the cellular composition has been treated with a reovirus prior to transplantation to remove neoplastic cells, wherein the transplantation is autologous, allogeneic or xenogeneic.

2. The cellular composition of claim 1, wherein the neoplastic cells are ras-mediated neoplastic cells.

3. The cellular composition of claim 1, wherein the cellular composition comprises hematopoietic stem cells.

4. The cellular composition of claim 3, wherein the hematopoietic stem cells are harvested from blood.

5. The cellular composition of claim 3, wherein the hematopoietic stem cells are harvested from bone marrow.

6. The cellular composition of claim 1, wherein the cellular composition comprises CD34+ stem cells.

7. The cellular composition of claim 1, wherein the cellular composition comprises a tissue, an organ or any portion of a tissue or organ.

8. The method of claim 7, wherein the tissue or organ is selected from the group consisting of liver, kidney, heart, cornea, skin, and lung.

9. The cellular composition of claim 1, wherein the cellular composition comprises pancreatic islet cells.

10. The cellular composition of claim 1, wherein the cellular composition is whole blood.

11. The cellular composition of claim 1, wherein the cellular composition comprises semen or eggs.

12. The cellular composition of claim 1, wherein the reovirus is a mammalian reovirus.

13. The cellular composition of claim 1, wherein the reovirus is a human reovirus.

14. The cellular composition of claim 1, wherein the human reovirus is selected from the group consisting of serotype 1 reovirus, serotype 2 reovirus and serotype 3 reovirus.

15. The cellular composition of claim 14, wherein the human reovirus is serotype 3 reovirus.

16. The cellular composition of claim 15, wherein the serotype 3 reovirus is reovirus strain Dearing.

17. The cellular composition of claim 1, wherein the reovirus is a recombinant reovirus.

18. The cellular composition of claim 1, wherein the reovirus is a modified reovirus.

19. The cellular composition of claim 1, wherein the composition is frozen and stored in a solution containing DMSO.

20. The cellular composition of claim 1, wherein the cellular composition has been further treated with an anti-reovirus antibody.

21. The cellular composition of claim 1, wherein the cellular composition has been further treated with anti-reovirus antibodies and complement.

22. The cellular composition of claim 1, wherein the cellular composition has been subjected to a gradient that separates the cells of the cellular composition from the reovirus and the reovirus has been removed.

* * * * *